(12) United States Patent
Huxel et al.

(10) Patent No.: US 7,507,247 B2
(45) Date of Patent: Mar. 24, 2009

(54) URETHRAL CATHETER STENT DELIVERY SYSTEM

(75) Inventors: Shawn T. Huxel, Lawrenceville, NJ (US); Todd Fruchterman, Yardley, PA (US); Mark Boomer, Providence, RI (US); Thomas M. Poandl, Metuchen, NJ (US); Ronald W. Marsh, Hackettstown, NJ (US)

(73) Assignee: Ethicon, Inc., Somerville, NJ (US)

( * ) Notice: Subject to any disclaimer, the term of this patent is extended or adjusted under 35 U.S.C. 154(b) by 592 days.

(21) Appl. No.: 11/151,046

(22) Filed: Jun. 13, 2005

(65) Prior Publication Data

US 2005/0234539 A1    Oct. 20, 2005

Related U.S. Application Data

(62) Division of application No. 10/256,609, filed on Sep. 27, 2002, now Pat. No. 6,929,651.

(51) Int. Cl.
*A61M 29/00*    (2006.01)

(52) U.S. Cl. .................................... 606/198; 623/23.66

(58) Field of Classification Search ................ 606/108, 606/191, 192, 194, 198; 623/1.11, 1.12, 623/23.64, 23.66, 23.7
See application file for complete search history.

(56) References Cited

U.S. PATENT DOCUMENTS

| | | | |
|---|---|---|---|
| 4,762,128 A * | 8/1988 | Rosenbluth | 606/192 |
| 4,893,623 A * | 1/1990 | Rosenbluth | 606/192 |
| 4,913,683 A | 4/1990 | Gregory | |
| 5,059,169 A | 10/1991 | Zilber | |
| 5,078,720 A | 1/1992 | Burton et al. | |
| 5,098,374 A | 3/1992 | Othel-Jacobsen et al. | |
| 5,322,501 A | 6/1994 | Mahmud-Durrani | |
| 5,591,199 A | 1/1997 | Porter et al. | |
| 5,667,486 A | 9/1997 | Mikulich et al. | |
| 5,667,522 A | 9/1997 | Flomenblit et al. | |
| 5,830,179 A | 11/1998 | Mikus et al. | |
| 5,928,217 A | 7/1999 | Mikus et al. | |
| 5,980,564 A | 11/1999 | Stinson | |
| 5,992,419 A | 11/1999 | Sterzer et al. | |
| 6,033,413 A | 3/2000 | Mikus et al. | |
| 6,119,045 A | 9/2000 | Bolmsjo | |
| 6,221,081 B1 | 4/2001 | Mikus et al. | |
| 6,338,739 B1 | 1/2002 | Datta et al. | |
| 6,770,101 B2 | 8/2004 | Desmond et al. | |
| 6,929,651 B2 | 8/2005 | Huxel et al. | |
| 2002/0035391 A1 | 3/2002 | Mikus et al. | |

FOREIGN PATENT DOCUMENTS

| | | |
|---|---|---|
| JP | 2003 052835 A | 2/2003 |
| WO | WO 95/23564 | 9/1995 |
| WO | WO 01/17459 A1 | 3/2001 |
| WO | WO 01/43664 A1 | 6/2001 |

OTHER PUBLICATIONS

European Search Report dated Feb. 27, 2004 for corresponding European Patent Application No. 3256081.5.

* cited by examiner

*Primary Examiner*—Kevin T Truong

(57) ABSTRACT

A stent delivery system for the placement of non-expandable stents in the urethra is described. The delivery system is generally composed of a catheter with a stent mounted near the distal end of the catheter. The stent is held in place by a balloon or mechanical mechanism.

20 Claims, 15 Drawing Sheets

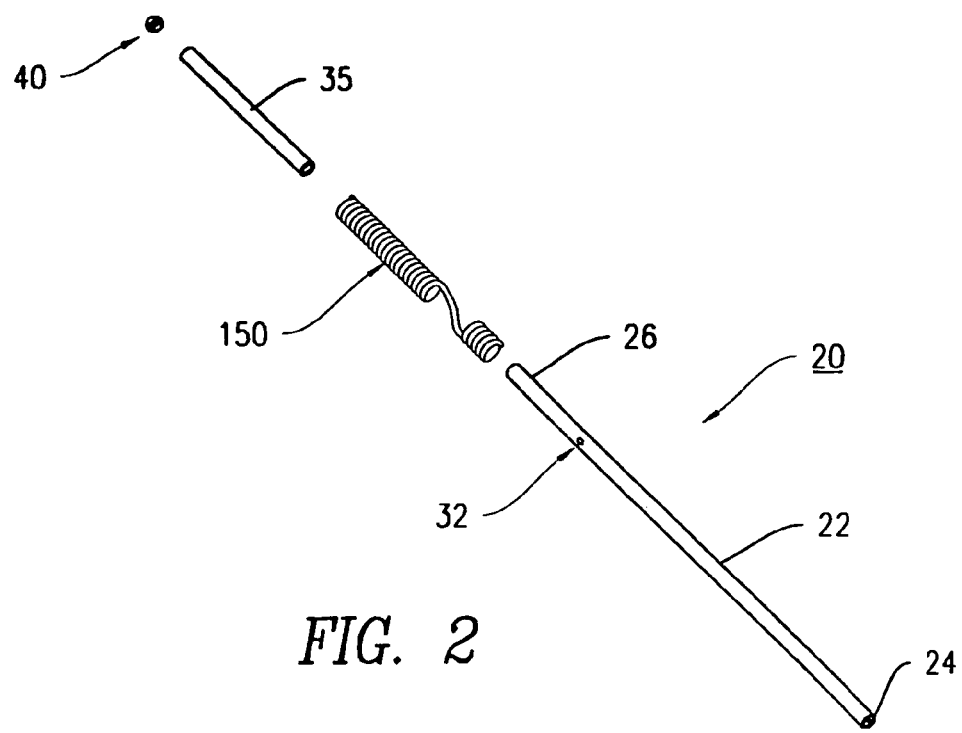
FIG. 2
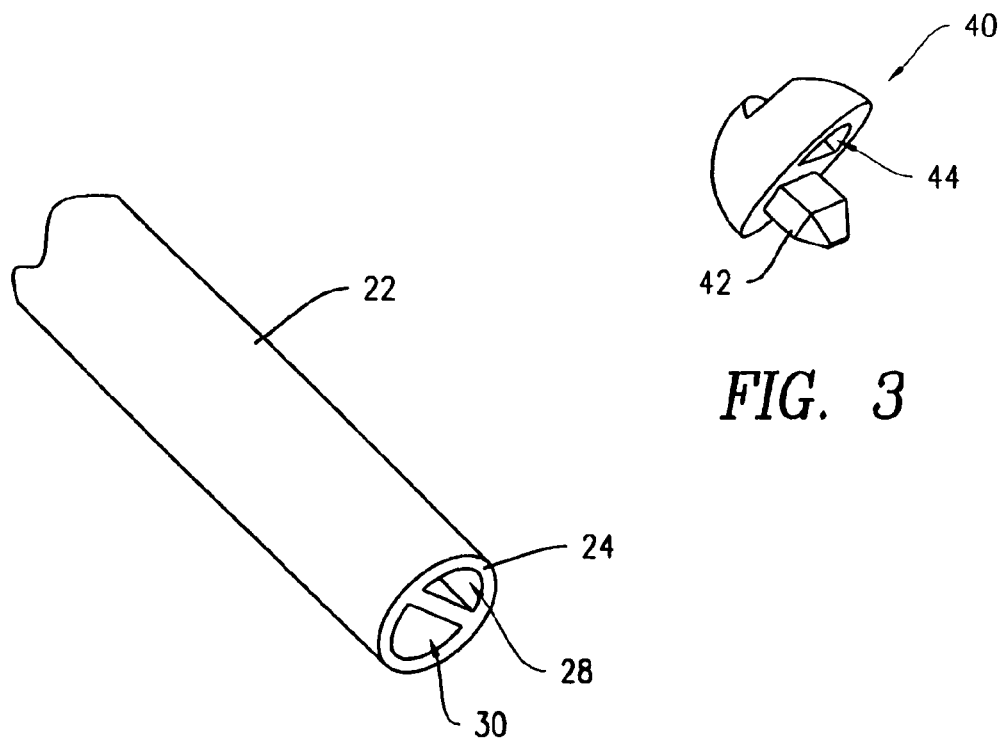
FIG. 3
FIG. 4

URETHRAL CATHETER STENT DELIVERY SYSTEM

CROSS REFERENCE TO RELATED APPLICATION

This application is a divisional of U.S. patent application Ser. No. 10/256,609, filed Sep. 27, 2002 now U.S. Pat. No. 6,929,651, the disclosure of which is incorporated herein by reference in its entirety.

FIELD OF THE INVENTION

This invention relates to stent delivery systems to facilitate the temporary relief of urinary retention caused by enlargement of the prostate gland or severe lower urinary tract symptoms.

BACKGROUND OF THE INVENTION

The prostate gland surrounds the prostatic urethra, and enlargement of the prostate gland prevents passage of urine from the bladder. Enlargement of the prostate gland can result from the following etiologies: 1) benign prostatic hyperplasia (BPH); 2) carcinoma of the prostrate; 3) prostatitis; 4) post-procedural edema; 5) prostatic trauma; as well as others. Prostatic enlargement, is a common affliction among men. Prostatic enlargement is uncomfortable because it makes urination difficult or impossible. The condition is also dangerous because it can lead to infection of the bladder and kidneys, and severe cases may lead to death.

Lower urinary tract symptoms (LUTS), also common among older men, comprise a variety of conditions which can also lead to urinary retention and other complications resulting from retention. Some of the conditions falling under LUTS diagnosis include an enlarged prostate, BPH, and bladder outlet obstruction.

Prostatic enlargement can be treated with the implantation of a prostatic urethral stent. The stent serves to hold open the prostatic urethra to facilitate fluid flow during urination. A stent may be implanted, or delivered, as an interim solution to hold open the prostatic urethra while the patient awaits corrective treatment A stent may be implanted after thermal therapy or cryosurgery to keep the urethra open while post-treatment edema subsides. A stent may be implanted after radiation to keep the urethra open as the radiation effects on the prostatic tissue subside. Finally, a stent may be implanted as a primary treatment.

There are many different types of urethral stents. Generally, they are tubular in shape, and may be composed of solid tubes, coiled wire or ribbon, mesh, or braided filaments. Many stents are inserted, or delivered, into the urethra in a radially compressed form by a stent delivery system. After being properly positioned, these types of stents are radially expanded into their final shape, typically by thermal or mechanical means.

There are also non-expandable stents that are inserted into the urethra in their final form by a stent delivery system. These stents have an advantage over expandable stents in that the final configuration of the stent is known at the time of stent insertion.

During the first steps of the stent deployment process, the stent must be held in place on the stent delivery system during insertion. For expandable stents, this is typically accomplished by placing the stent inside a sheath, by crimping onto a catheter balloon, or by using a mechanical retainer or stopper.

Non-expandable stents are held in place on the stent delivery system by means of flexible tether strings (see U.S. Pat. No. 5,322,501 to Mahmud-Durrani) or a coiled wire fastening element (see U.S. Pat. No. 5,098,374 to Orthel-Jacobsen, et al.).

In the case of the Mahmud-Durrani delivery system, the stent is retained within the prostatic urethra by the same flexible tether strings, connected to a locating member. The locating member remains in the bladder as an anchoring means after the stent is delivered.

In the Orthel-Jacobsen delivery system, the coiled wire fastening element must be rotated by over 900 degrees in a screwing movement to release the stent from the fastening element.

Another consideration for urethral stent delivery is that it is usually better to deliver the stent to a location which allows uncompromised function of the bladder neck sphincter and the external sphincter. These sphincters control the flow of urine through the urethra. Obstruction of these sphincters leads to incontinence. To ensure the proper positioning of the stent, a number of prior art stent delivery systems provide position systems including visualization of the bladder and prostatic urethra during placement, mechanically locating off of the bladder neck, and anchoring of the stent delivery system in place during insertion.

In summary, prostatic enlargement is a common affliction among men. The symptoms of prostatic enlargement can be treated with the implantation of a urethral stent, which holds open the urethra to facilitate fluid flow during urination. Both expandable and non-expandable urethral stents have been used. The known final dimension of the non-expandable stents is a desirable feature. However, simple means for holding the non-expandable stent on the stent delivery system, and a simple method of deployment of non-expandable stents is desired.

SUMMARY OF THE INVENTION

The stent delivery system described below permits placement of stents in the prostatic urethra. The delivery system is intended to deploy a non-expandable stent into the urethra. This is accomplished by disposing the stent delivery system in the urethra such that the non-expandable stent is located in the prostatic urethra, releasing the non-expandable stent from the stent delivery system, and removing the stent delivery system from the urethra.

The device may be provided as a disposable item that is generally composed of a catheter with a stent mounted near the distal end of the catheter. The stent is held in place by a balloon or mechanical mechanism.

In a preferred embodiment, surgeons who use the disclosed stent delivery system can also be sure that the stent does not block the bladder neck sphincter. This is accomplished by disposing the stent delivery system in the urethra, temporarily anchoring the stent delivery system within the bladder neck such that the non-expandable stent is located in the prostatic urethra, releasing the non-expandable stent from the stent delivery system, releasing the stent delivery system anchor from the bladder neck, and removing the stent delivery system from the urethra.

The preferred embodiment device may be provided as a disposable item which is generally composed of a catheter with a locating balloon or mechanical mechanism attached at its distal end which serves to anchor the device in place and locate the bladder neck, and a stent mounted proximal to the locating balloon or mechanical mechanism. The stent is held in place by a separate retention balloon or mechanical mechanism.

BRIEF DESCRIPTION OF THE FIGURES

The novel features of the present invention will be more readily apparent upon reading the following description in conjunction with the drawings in which like elements in different figures are identified by the same reference numeral and wherein:

FIG. 2 shows an exploded view of a first embodiment of the inventive stent delivery system;

FIG. 3 shows a perspective view of the distal tip of the first embodiment of the stent delivery system;

FIG. 4 shows a perspective view of the proximal end of the catheter of the first embodiment of the stent delivery system;

DETAILED DESCRIPTION OF THE INVENTION

Figure 1:
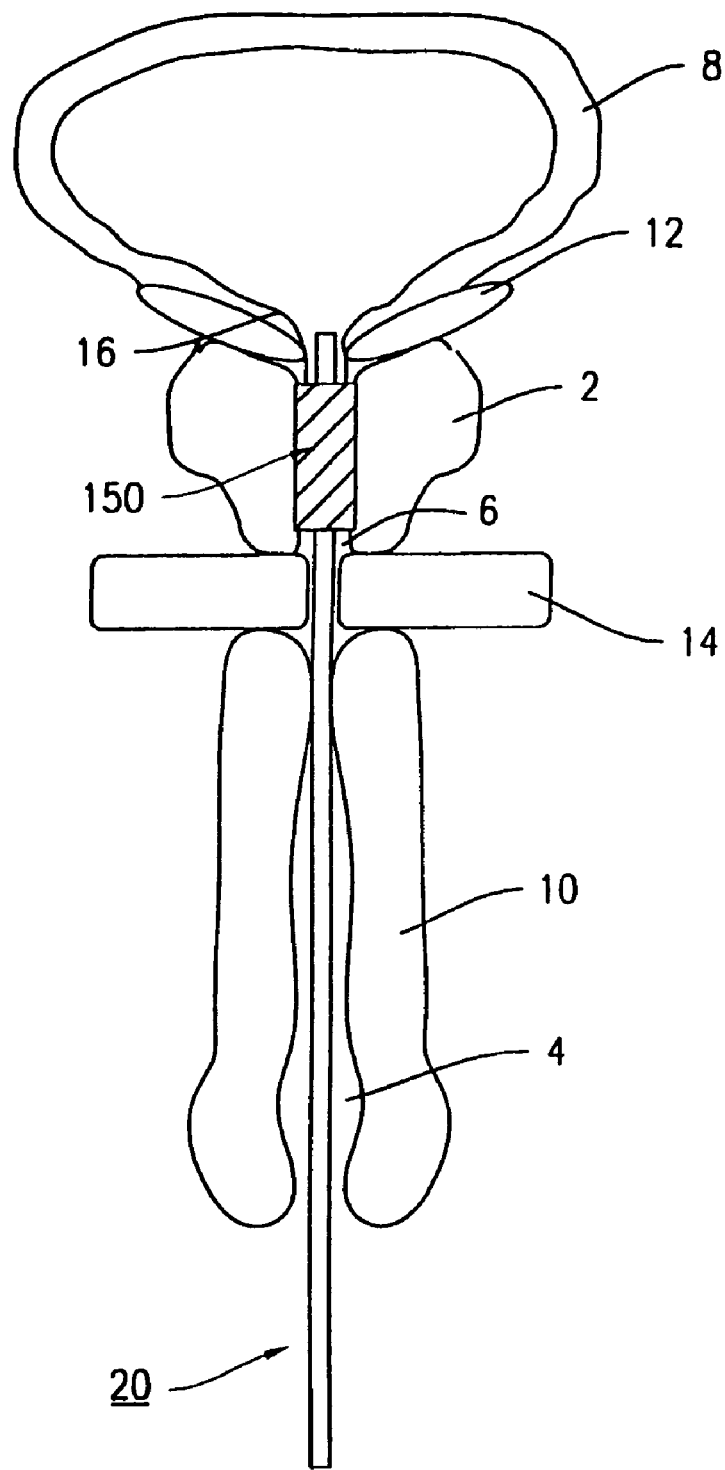
FIG. 1 is a cross-sectional view of the lower abdominal portion of the human male anatomy with a stent delivery system in place.

FIG. 1 shows a schematic representation of the stent delivery system 20 designed for use in the treatment of benign prostate hyperplasia, prostate cancer, or LUTS in place within the human male anatomy. The details of the local anatomy shown in FIG. 1 include the prostate gland 2, the penile urethra 4, the prostatic urethra 6, and the bladder 8. The penile urethra 4 is the channel that conducts urine from the bladder 8 through the penis 10 for discharge from the body. The prostatic urethra 6 is the portion of the urethra located within the prostate gland 2. The bladder neck sphincter 12 controls flow of urine from the bladder 8 through the bladder neck 16. The external sphincter 14 controls flow of urine or ejaculate from the prostatic urethra 6 to the penile urethra 4. The inside diameter of penile urethra 4 is typically about 2 cm, and the prostatic urethra 6 varies in length from about 15 to 75 mm.

Stent 150 is placed in prostatic urethra 6 to hold open prostatic urethra 6 to facilitate fluid flow during urination. Stent 150 is shown throughout this document as a device with generally cylindrical geometry. More specifically, stent 150 is shown as the coiled wire structure reported in U.S. Pat. No. 6,338,739, issued Jan. 15, 2002 from U.S. patent application Ser. No. 09/470,619, entitled "Biodegradable stent", assigned to Ethicon incorporated and incorporated herein by reference. However, one trained in the art could see that other stent constructs could also be used with the stent delivery system of the current invention.

Stent 150 is delivered to the prostatic urethra 6 by the stent delivery system 20 illustrated in the following figures. A first embodiment of the present invention is shown on FIGS. 2-7. The stent delivery system 20 generally includes catheter 22, distal tip 40, and stent retention balloon 35.

Catheter 22 is a tubular structure with proximal 24 and distal 26 ends, through-lumen 28, stent retention balloon lumen 30, and stent retention balloon port 32. Distal tip 40, disposed on catheter distal end 26, has tip lumen seal protrusion 42 and tip through-hole 44. Distal tip 40 is disposed on catheter distal end 26 so that tip lumen seal protrusion 42 is disposed in stent retention balloon lumen 30 to seal the lumen, and tip through-hole 44 is aligned with through-lumen 28. In practice, tip through-hole 44 and through-lumen 28 allow passage of either a guide wire, or a visualization means to facilitate delivery system placement, through catheter 22 to allow for accurate placement of stent 150 in prostatic urethra 6.

Alternatively, distal tip blunting and lumen sealing to seal stent retention balloon lumen 30 can also be accomplished by thermal/RF forming and lumen potting.

Figure 5:
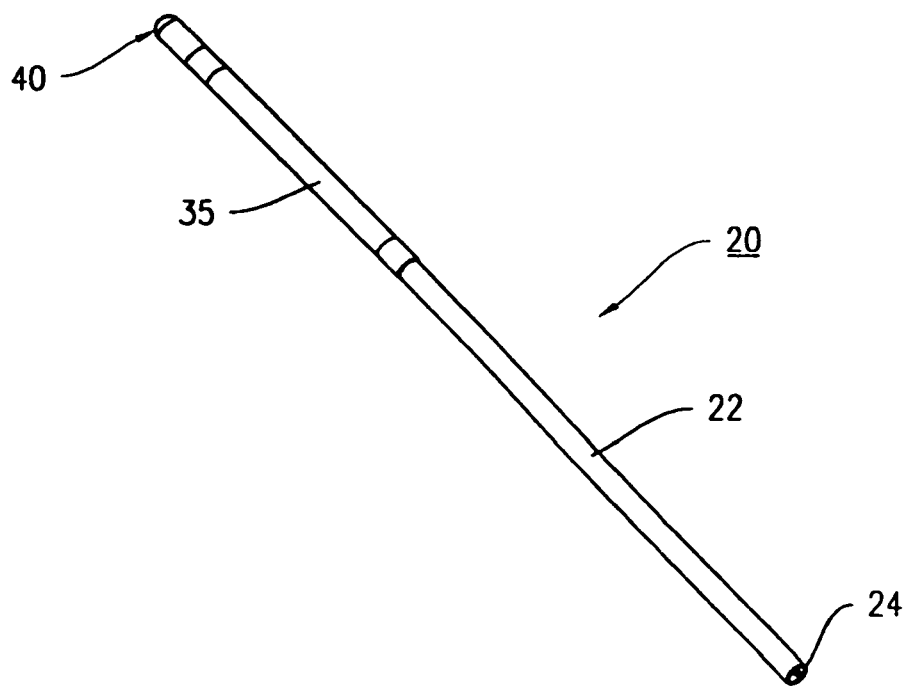
FIG. 5 shows a perspective assembly view of the first embodiment of the stent delivery system.
Figure 6:
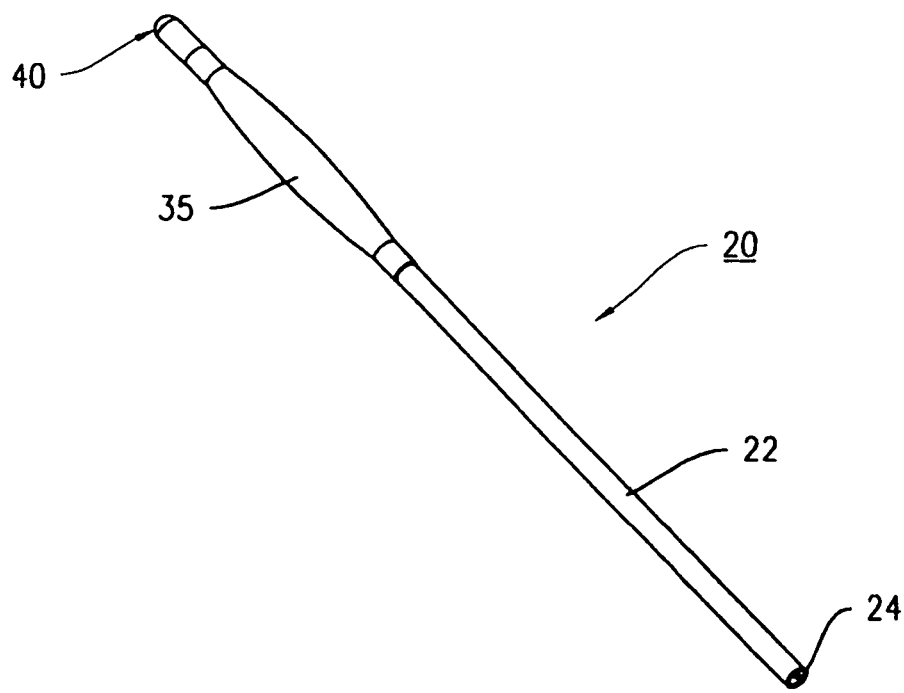
FIG. 6 shows a perspective view of the first embodiment of the stent delivery system with the stent retention balloon inflated.

Stent retention balloon 35 is disposed on catheter 22 so that stent retention balloon port 32 is covered by stent retention balloon 35 approximately centered with respect to one another. Tip lumen seal protrusion 42 seals stent retention balloon lumen 30 so that when pressurized gas, such as air, or a fluid such as saline, is introduced into stent retention balloon lumen 30, the gas or fluid passes through stent retention balloon port 32 and stent retention balloon 35 is inflated. FIGS. 5 and 6 show stent retention balloon 35 in both deflated and inflated states, respectively.

Figure 7:
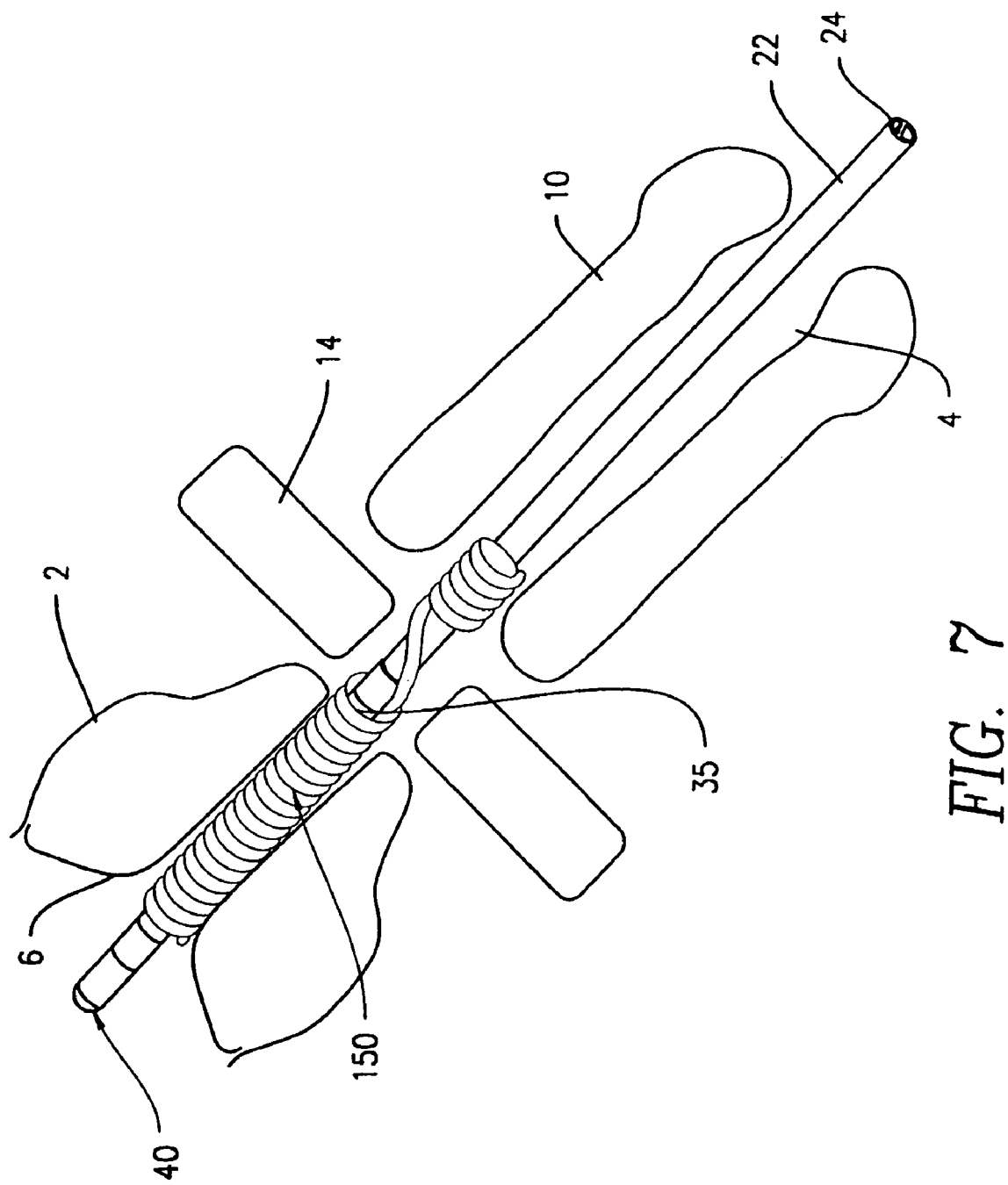
FIG. 7 shows a view of the lower abdominal portion of the human male anatomy with the first embodiment of the stent delivery system in place.
Figure 8:
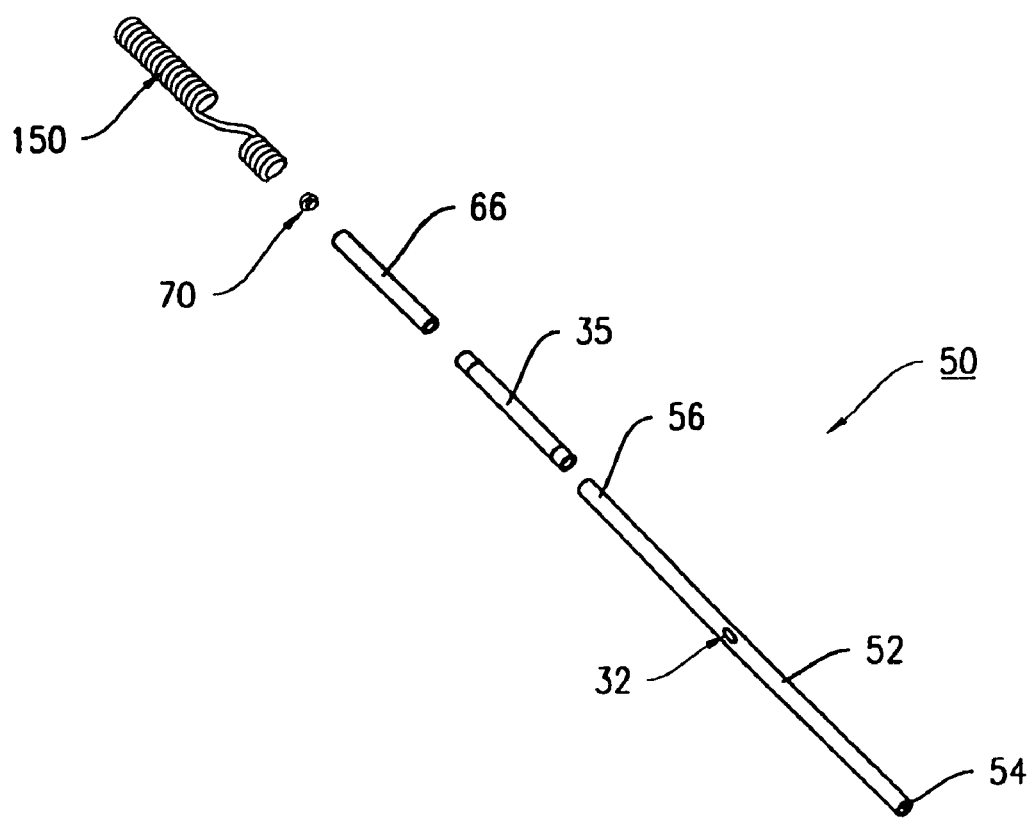
FIG. 8 shows an exploded view of a second embodiment of the stent delivery system.

The procedure for using stent delivery system 20 to implant stent 150 into the prostatic urethra 6 to maintain urethral patency is initiated by disposing stent 150 over a deflated stent retention balloon 35. Stent retention balloon 35 is then inflated as discussed above to hold stent 150 on stent delivery system 20. Stent delivery system 20 is inserted through the penile urethra 4 until stent 150 is located in the prostatic urethra 6 as shown in FIG. 7. Stent retention balloon 35 is then deflated. This releases stent 150 from stent delivery system 20 without changing the dimensions of stent 150. Stent delivery system 20 is removed from the prostatic 6 and penile 4 urethrae, leaving stent 150 in prostatic urethra 6.

As previously mentioned, tip through-hole 44 and through-lumen 28 allow passage of either a guide wire, or a visualization means to facilitate delivery system placement, through catheter 22 to allow for accurate placement of stent 150 in prostatic urethra 6. A second embodiment stent delivery system 50, as shown in FIGS. 8 to 14, could also be used to accurately place stent 150 in prostatic urethra 6. Stent delivery system 50 generally includes catheter 52, distal tip 70, stent retention balloon 35, and locating balloon 66.

Catheter 52 is a tubular structure with proximal 54 and distal 56 ends, stent retention balloon lumen 58, locating balloon lumen 60, stent retention balloon port 32, and locating balloon port 64. Distal tip 70, disposed on catheter distal end 56, has tip lumen seal protrusions 74,76. Distal tip 70 is disposed on catheter distal end 56 so that tip lumen seal protrusions 74,76 are disposed in stent retention balloon lumen 58 and locating balloon lumen 60, respectively, to seal these lumen. Distal tip blunting or lumen sealing may also be used to seal these lumens.

Figure 11:
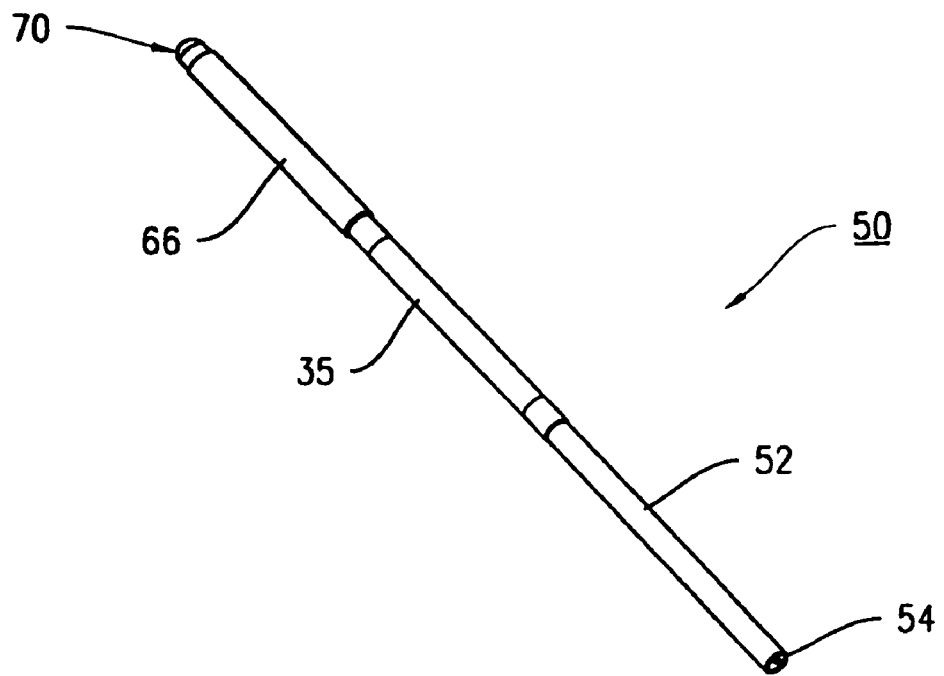
FIG. 11 shows a perspective assembly view of the second embodiment of the stent delivery system.
Figure 12:
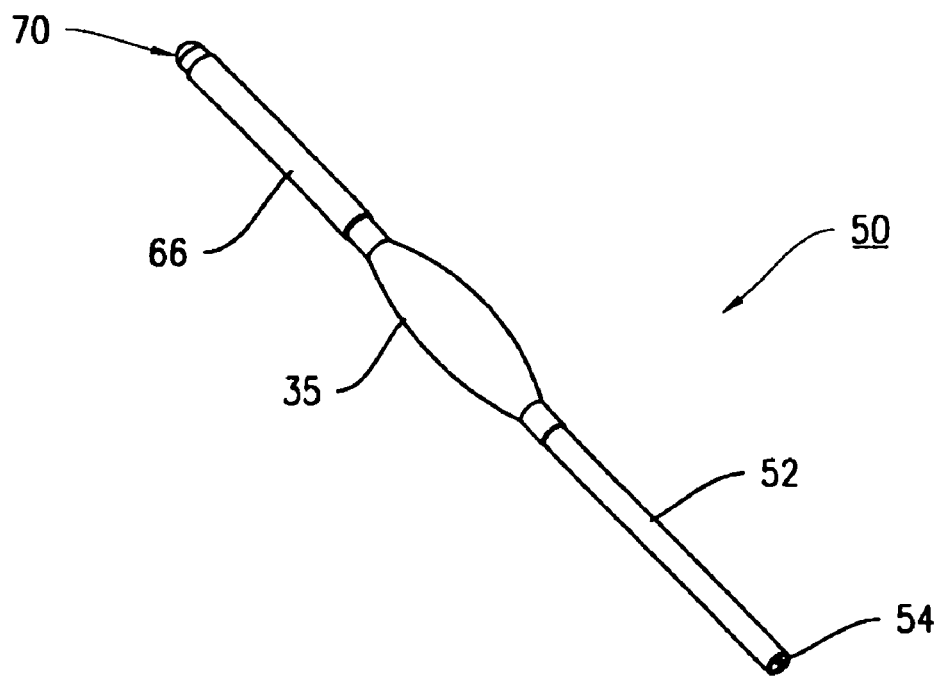
FIG. 12 shows a perspective assembly view of the second embodiment of the stent delivery system with the stent retention balloon inflated.

Stent retention balloon 35 is disposed on catheter 52 so that stent retention balloon port 32 is covered by stent retention balloon 35. Tip lumen seal protrusion 74 seals stent retention balloon lumen 58 so that when pressurized gas, such as air, or a fluid such as saline, is introduced into stent retention balloon lumen 58, the gas or fluid will pass through stent retention balloon port 32 to inflate stent retention balloon 35. FIGS. 11 and 12 show stent retention balloon 35 in both deflated and inflated states, respectively.

Locating balloon 66 is disposed on catheter 52 so that locating balloon port 64 is covered by locating balloon 66 roughly centered with respect to one another. Tip lumen seal protrusion 76 seals locating balloon lumen 60 so that when pressurized gas is introduced into locating balloon lumen 60, the gas or fluid will pass through locating balloon port 64 to inflate locating balloon 66.

Figure 13:
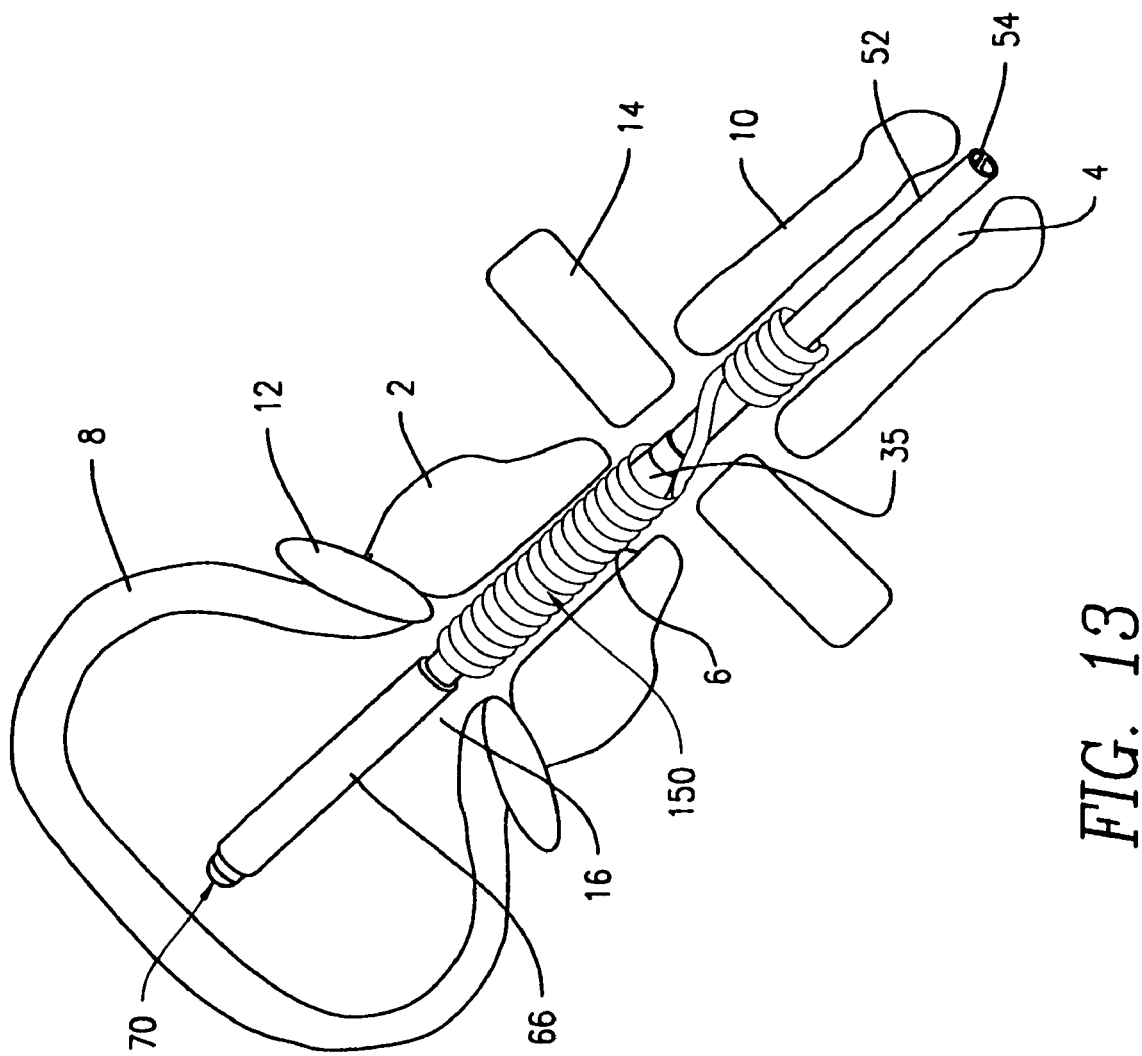
FIG. 13 shows a view of the lower abdominal portion of the human male anatomy with the second embodiment of the stent delivery system in place.

The procedure for using stent delivery system 50 to implant stent 150 into the prostatic urethra 6 to maintain urethral patency is initiated by disposing stent 150 over a deflated stent retention balloon 35. Stent retention balloon 35 is then inflated to hold stent 150 on stent delivery system 50. Stent delivery system 50 is inserted through the penile urethra 4 until stent 150 is located in the prostatic urethra 6, and locating balloon 66 is located in bladder 8. This is shown in FIG. 13.

Figure 14:
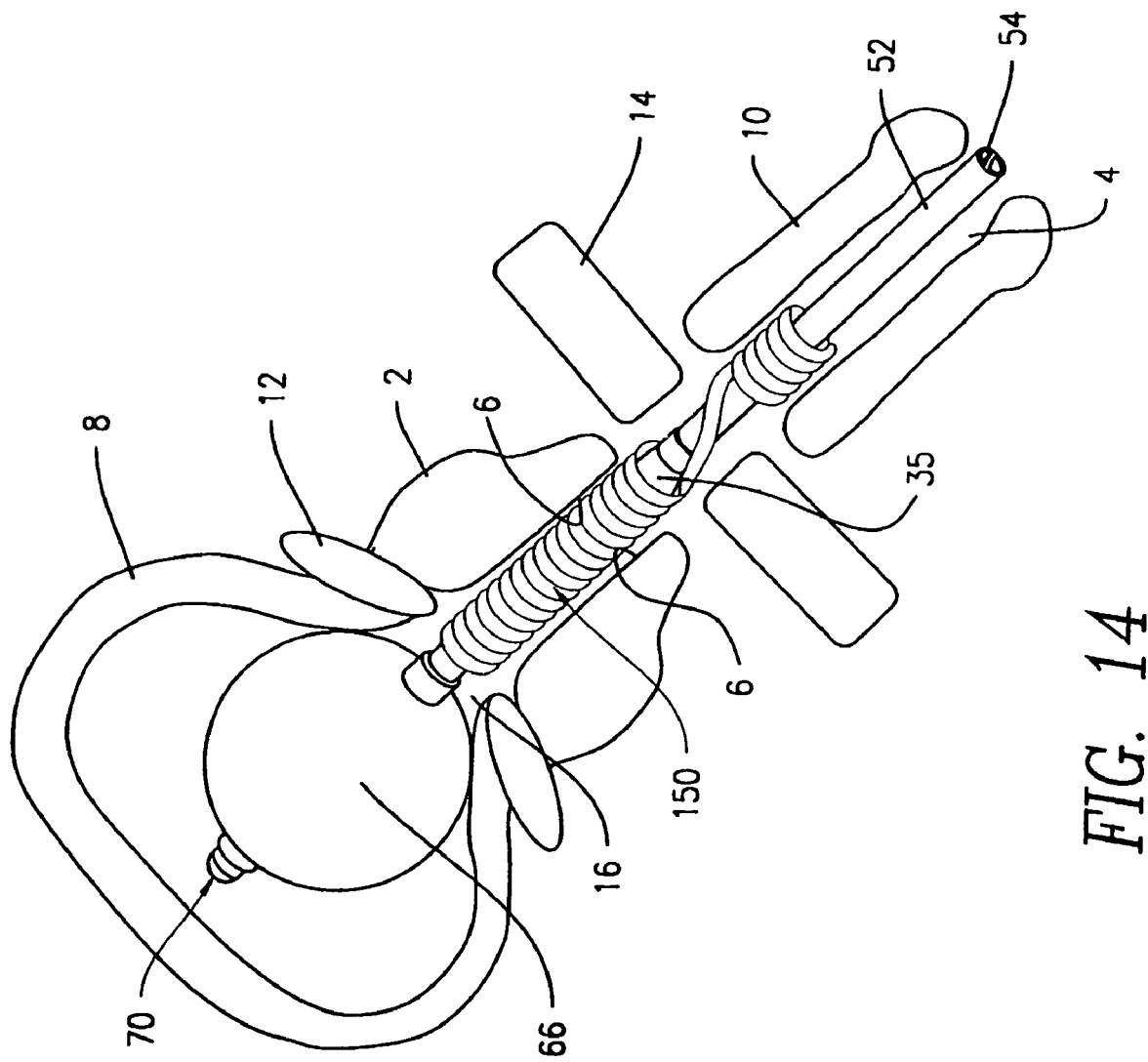
FIG. 14 shows a view of the lower abdominal portion of the human male anatomy with the second embodiment of the stent delivery system in place with the locating balloon inflated.

Locating balloon 66 is then inflated, and stent delivery system 50 is withdrawn and disposed so that locating balloon 66 is seated at bladder neck 16, as shown in FIG. 14. The locating balloon 66 is affixed to catheter 52 at an appropriate distance from stent retention balloon 35 so that the seating of locating balloon 66 at bladder neck 16 assures proper placement of stent 150 in prostatic urethra 6. Stent retention balloon 35 is then deflated. This releases stent 150 from stent delivery system 50 without changing the dimensions of stent 150. Locating balloon 66 is then deflated. Stent delivery system 50 is removed from the prostatic 6 and penile 4 urethra, leaving stent 150 in prostatic urethra 6.

Alternatively, stent retention balloon 35, as well as locating balloon 66 may be deflated simultaneously. This would also release stent 150 from stent delivery system 50 without changing the dimensions of stent 150. Stent delivery system 50 is then removed from the prostatic 6 and penile 4 urethra, leaving stent 150 in prostatic urethra 6.

Figure 15:
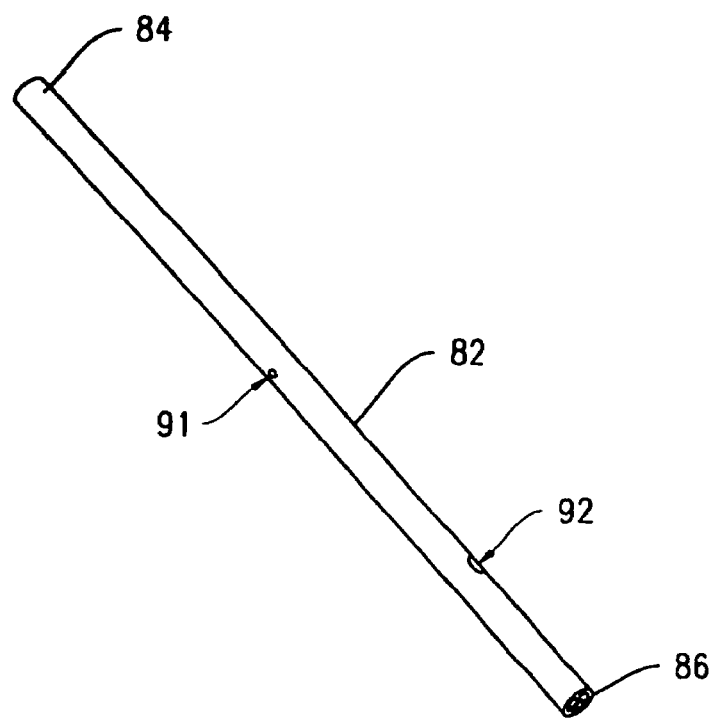
FIG. 15 shows a perspective view of the catheter of a third embodiment of the stent delivery system.
Figure 16:
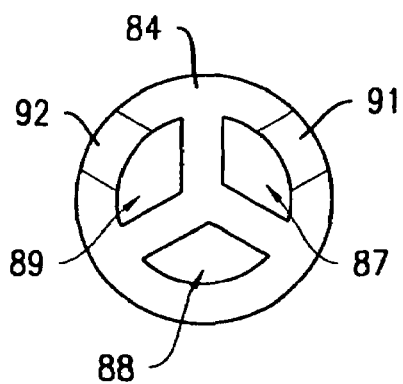
FIG. 16 shows an end view of the proximal end of the catheter of the third embodiment of the stent delivery system.
Figure 17:
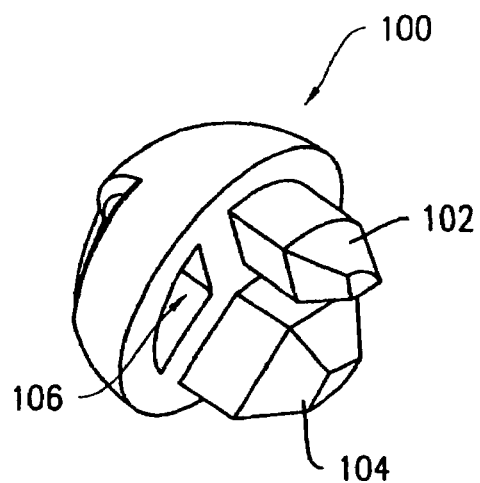
FIG. 17 shows a perspective view of the distal tip of the third embodiment of the stent delivery system.
Figure 18:
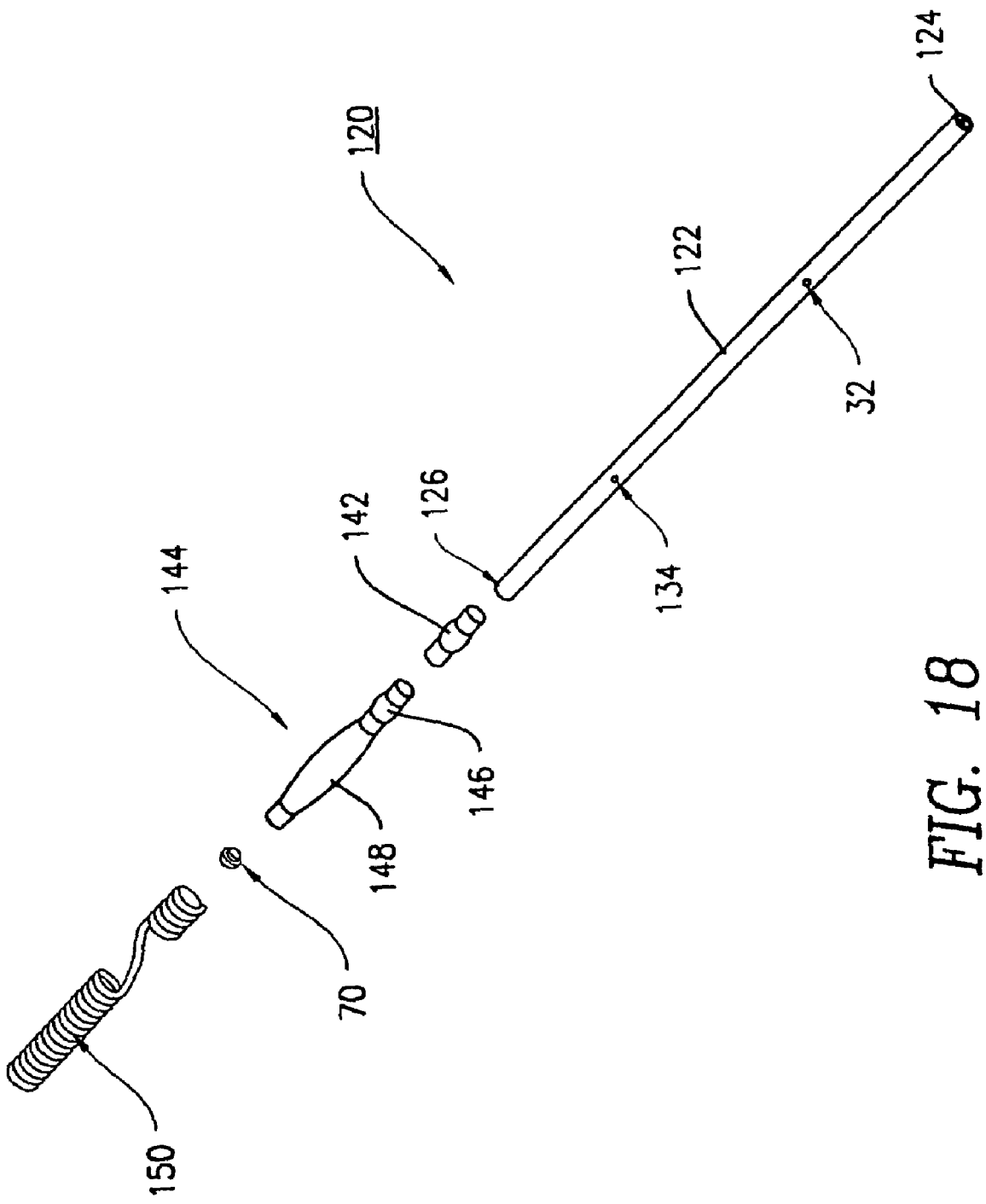
FIG. 18 shows an exploded view of a fourth embodiment of the stent delivery system.

Although this embodiment of the stent delivery system of the current invention allows for accurate placement of stent 150 in prostatic urethra 6, the user of the stent delivery system of the current invention may still wish to exercise an over-the-wire guidewire placement technique or direct visualization to place stent 150. A third embodiment of a catheter 82 and distal tip 100, shown in FIGS. 15 to 17, will allow for this capability.

Catheter 82 is a tubular structure with proximal 84 and distal 86 ends, stent retention balloon lumen 87, locating balloon lumen 89, through-lumen 88, stent retention balloon port 91, and locating balloon port 92. Distal tip 100, disposed on catheter distal end 86, has tip lumen seal protrusions 102,104, and tip through-hole 106. Distal tip 100 is disposed on catheter distal end 86 so that tip lumen seal protrusions 102,104 are respectively disposed in stent retention balloon lumen 87 and locating balloon lumen 89 to seal, and tip through-hole 106 is aligned with through-lumen 88. In practice, tip through-hole 106 and through-lumen 88 allow passage of either a guide wire, or a visualization means to facilitate delivery system placement, through catheter 82 to allow for accurate placement of stent 150 in prostatic urethra 6.

In each of the stent delivery system embodiments shown so far, stent 150 is held onto the delivery system by radial pressure and a frictional fit between stent 150 and stent retention balloon 35. In a fourth embodiment of the stent delivery system, shown in FIGS. 18 to 21, stent 150 is held on to delivery system by all or a portion of stent 150 captured between retention balloons at each end of stent 150. This stent delivery system 120 generally includes catheter 122, distal tip 70, proximal stent retention balloon 142, and distal balloon 144.

Figure 9:
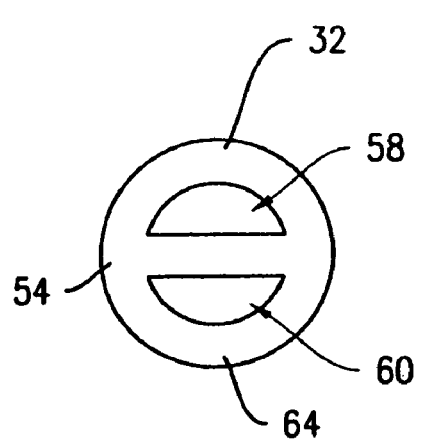
FIG. 9 shows an end view of the proximal end of the catheter of the second embodiment of the stent delivery system.
Figure 10:
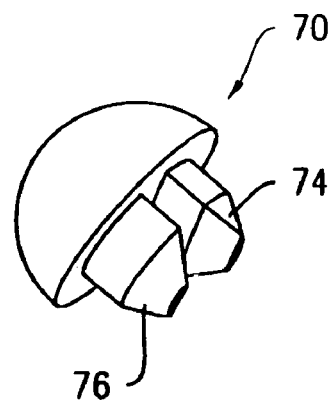
FIG. 10 shows a perspective view of the distal tip of the second embodiment of the stent delivery system.

Catheter 122 is a tubular structure with proximal 124 and distal 126 ends, stent retention balloon ports 32,134, and, as seen on FIG. 9, stent retention balloon lumen 58, locating balloon lumen 60, and locating balloon port 64. Distal tip 70, shown on FIG. 10, is disposed on catheter distal end 126, and has tip lumen seal protrusions 74,76. Distal tip 70 is disposed on catheter distal end 126 so that tip lumen seal protrusions 74,76 are respectively disposed in stent retention balloon lumen 58 and locating balloon lumen 60 to seal.

Distal balloon 144 has two balloon chambers, distal stent retention balloon 146, and locating balloon 148, and is affixed to catheter 122 at both ends and between the two chambers.

Proximal stent retention balloon 142 and distal balloon 144 are disposed on catheter 122 so that stent retention balloon port 32 is covered by proximal stent retention balloon 142, and stent retention balloon port 134 is covered by distal stent retention balloon 146. Tip lumen seal protrusion 74 seals stent retention balloon lumen 58 so that when pressurized gas, such as air, or a fluid such as saline, is introduced into stent retention balloon lumen 58, the gas or fluid will pass through stent retention balloon ports 32 and 134 to inflate proximal 142 and distal 146 stent retention balloons.

Figure 19:
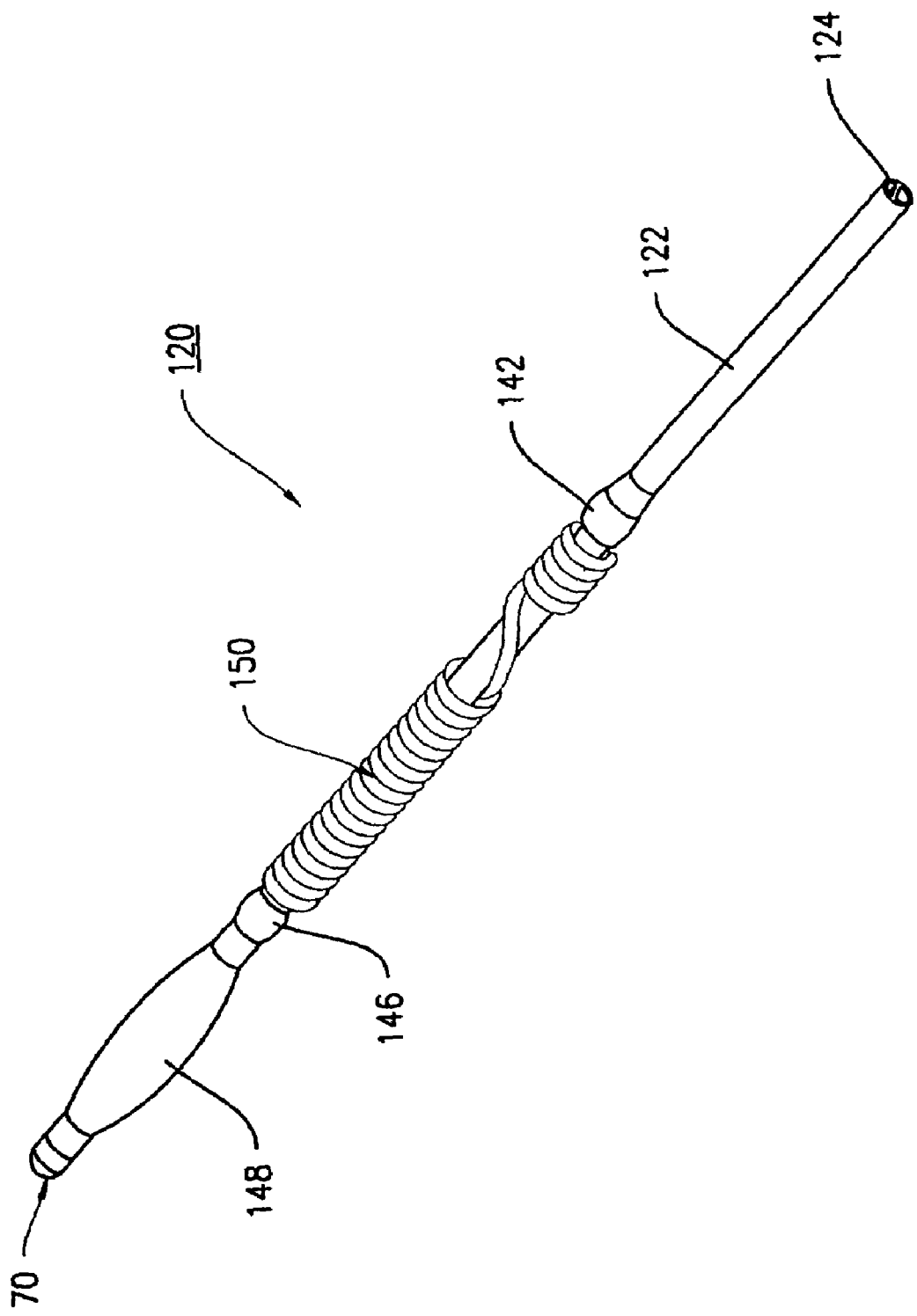
FIG. 19 shows a perspective assembly view of the fourth embodiment of the stent delivery system.
Figure 20:
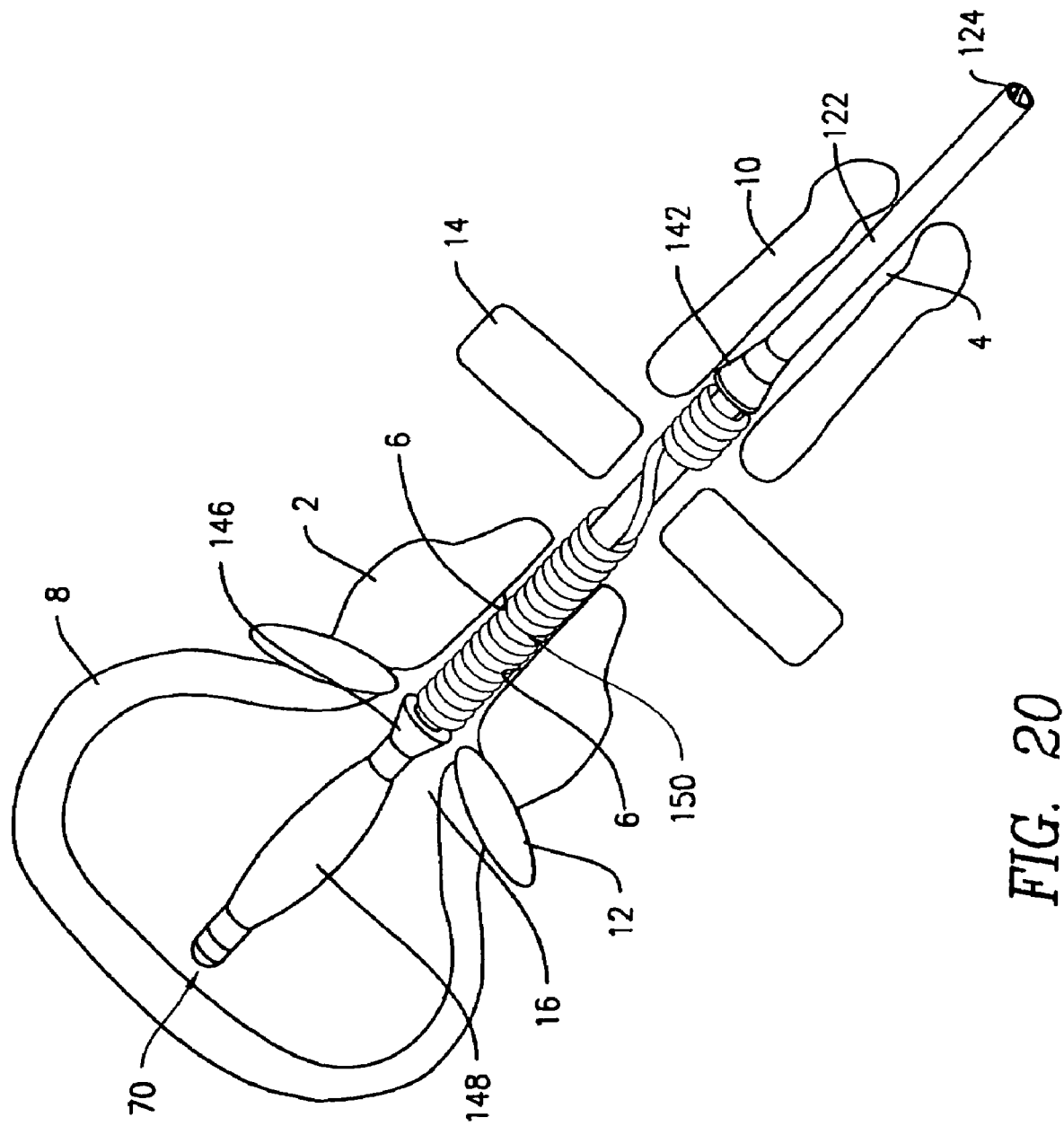
FIG. 20 shows a view of the lower abdominal portion of the human male anatomy with the fourth embodiment of the stent delivery system in place.

FIG. 19 shows stent delivery system 120 when assembled, with stent 150 disposed on stent delivery system 120 between proximal 142 and distal 146 stent retention balloons.

Locating balloon 148 is disposed on catheter 122 so that locating balloon port 64 is covered by locating balloon 148. Tip lumen seal protrusion 76 seals locating balloon lumen 60 so that when pressurized gas, such as air, or a fluid such as saline, is introduced into locating balloon lumen 60, the gas or fluid will pass through locating balloon port 64 to inflate locating balloon 148.

The procedure for using stent delivery system 120 to implant stent 150 into the prostatic urethra 6 to maintain urethral patency is initiated by disposing stent 150 on catheter 122, with all, or a portion of stent 150 located between proximal 142 and distal 146 stent retention balloons. Proximal 142 and distal 146 stent retention balloons are then inflated to hold stent 150 on stent delivery system 120. Stent delivery system 120 is inserted through the penile urethra 4 until stent 150 is located in the prostatic urethra 6, and locating balloon 148 is located in bladder 8. This is shown on FIG. 20.

Figure 21:
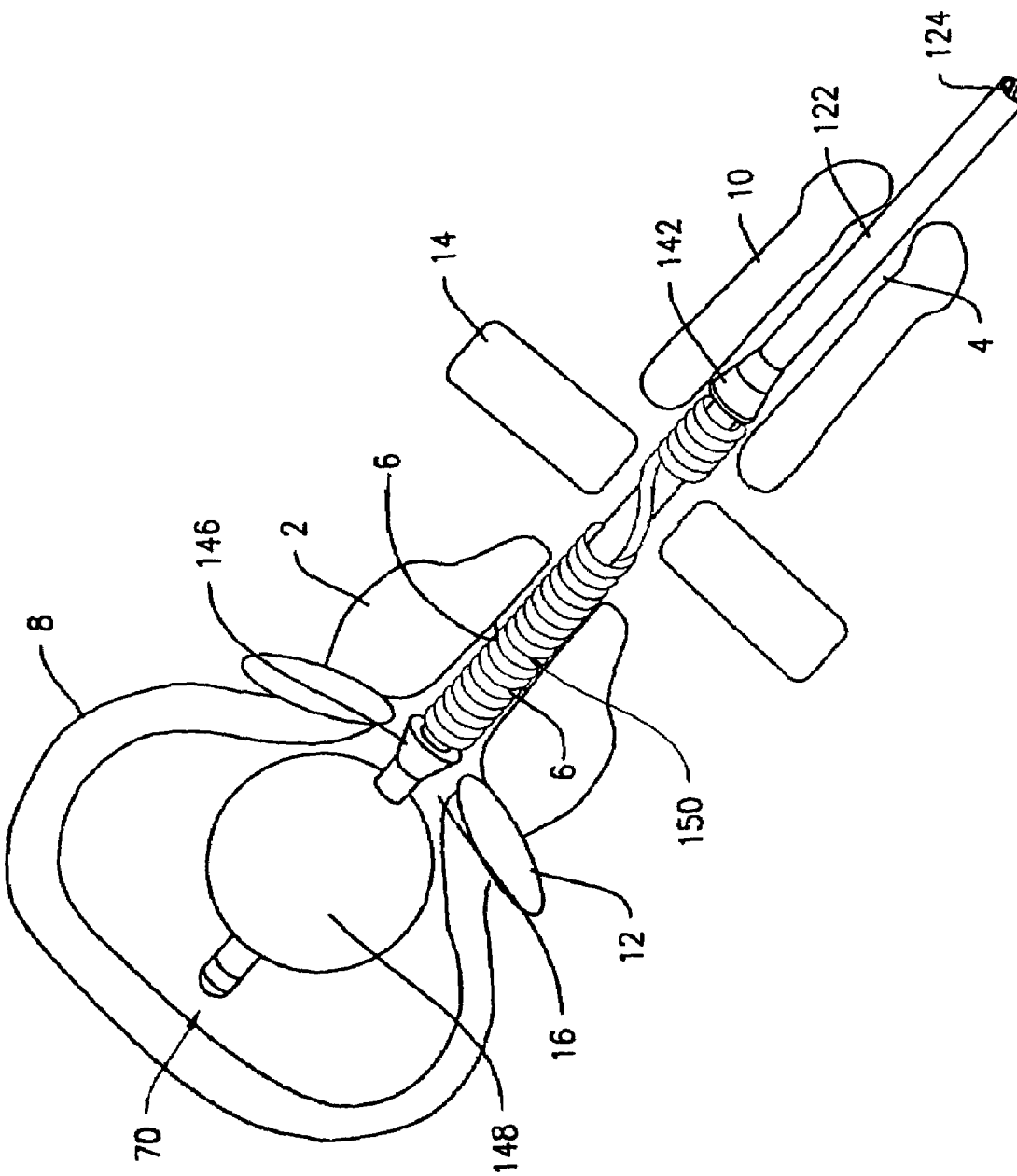
FIG. 21 shows a view of the lower abdominal portion of the human male anatomy with the fourth embodiment of the stent delivery system in place with the locating balloon inflated.

Locating balloon 148 is then inflated, and stent delivery system 120 is withdrawn and disposed so that locating balloon 148 is seated at bladder neck 16, as shown in FIG. 21. The locating balloon 148 is affixed to catheter 122 at an appropriate distance from distal stent retention balloon 146 so that the seating of locating balloon 148 in bladder neck 16 assures proper placement of stent 150 in prostatic urethra 6. Proximal 142 and distal 146 stent retention balloons are then deflated. This releases stent 150 from stent delivery system 120 without changing the dimensions of stent 150. Locating balloon 148 is then deflated. Stent delivery system 120 is removed from the prostatic 6 and penile 4 urethra, leaving stent 150 in prostatic urethra 6.

Alternatively, proximal 142 and distal 146 stent retention balloons, as well as locating balloon 148 may be deflated simultaneously. This would also release stent 150 from stent delivery system 120 without changing dimensions of stent 150. Stent delivery system 120 is then removed from the prostatic 6 and penile 4 urethra, leaving stent 150 in prostatic urethra 6.

Figure 22:
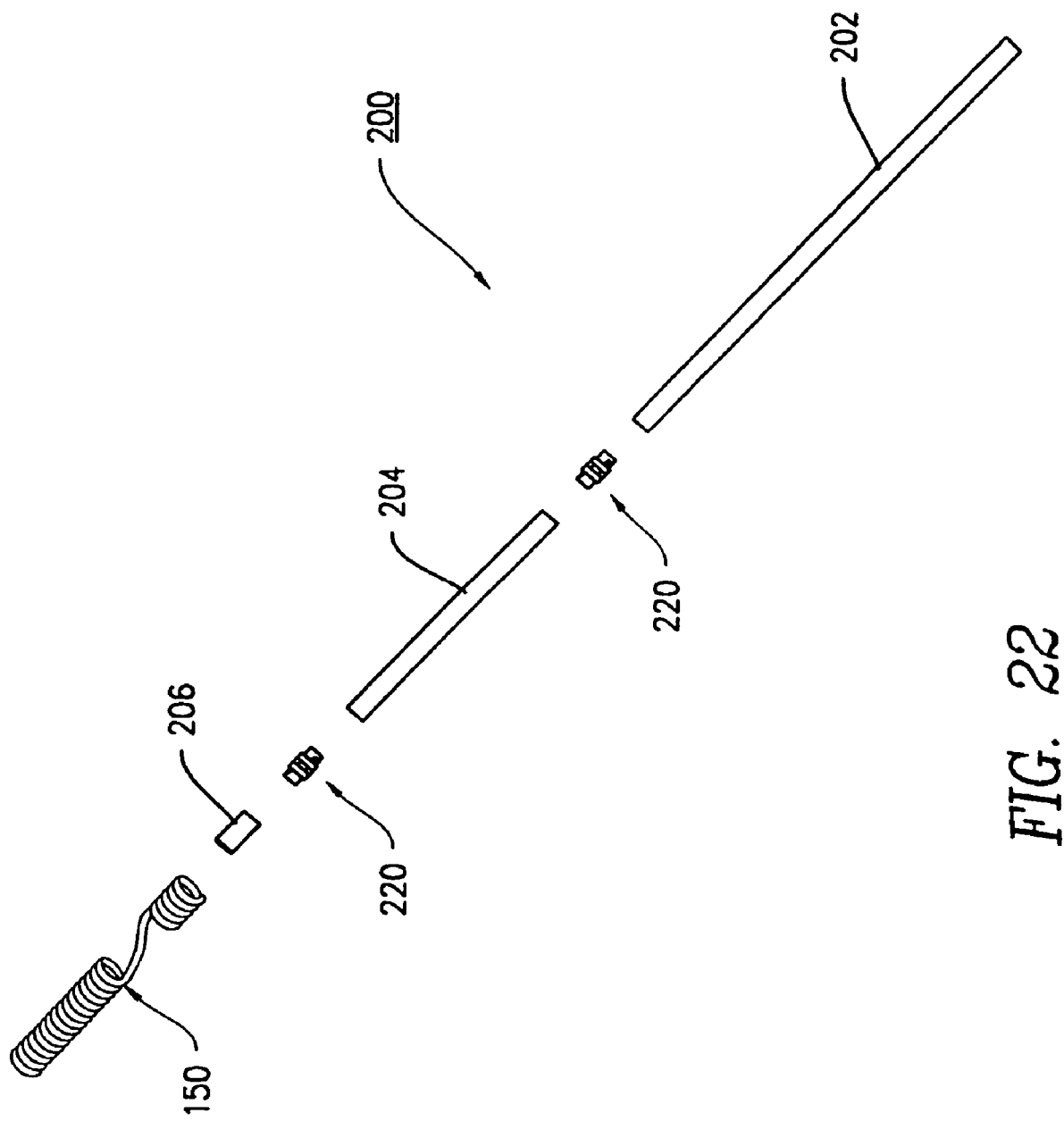
FIG. 22 shows an exploded view of a fifth embodiment of the stent delivery system.

In each delivery system discussed to this point, balloons have been used as the means for holding the sent on the delivery system. As previously discussed, these means may also be mechanical. Such an embodiment is shown on FIGS. 22 to 24, where stent 150 is held on to delivery system by all or a portion of stent 150 captured between retaining mechanisms at each end of stent 150. This stent delivery system 200 generally includes catheter proximal portion 202, catheter central portion 204, catheter distal portion 206, and mechanical retaining mechanisms 220.

Catheter portions 202,204,206 are tubular structures which are connected by mechanical retaining mechanisms 220. Mechanical retaining mechanisms 220 comprise proximal 222 and distal 224 couplers with through-holes 226,228, respectively, and radial retention members 230. Each radial retention member 230 has a deployment ramp 232. When a deployment rod, a catheter, or a scope passes through through-holes 226,228 of proximal 222 and distal 224 couplers, the rod will contact the deployment ramps 232, and radially displace the radial retention members 230.

Figure 23:
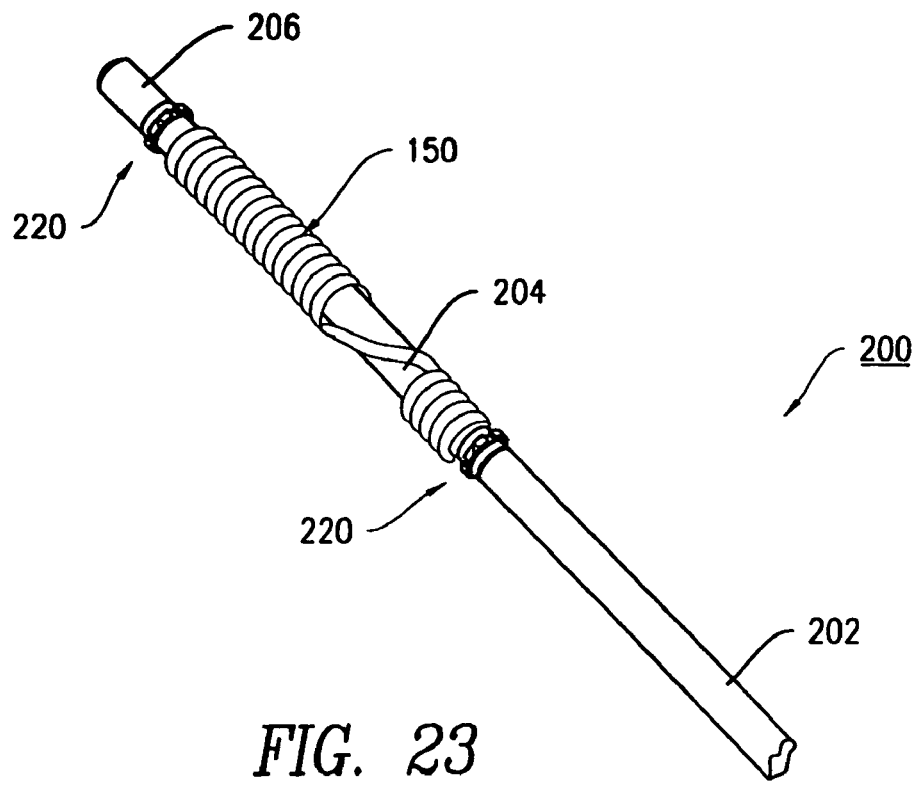
FIG. 23 shows a perspective assembly view of the fifth embodiment of the stent delivery system.
Figure 24:
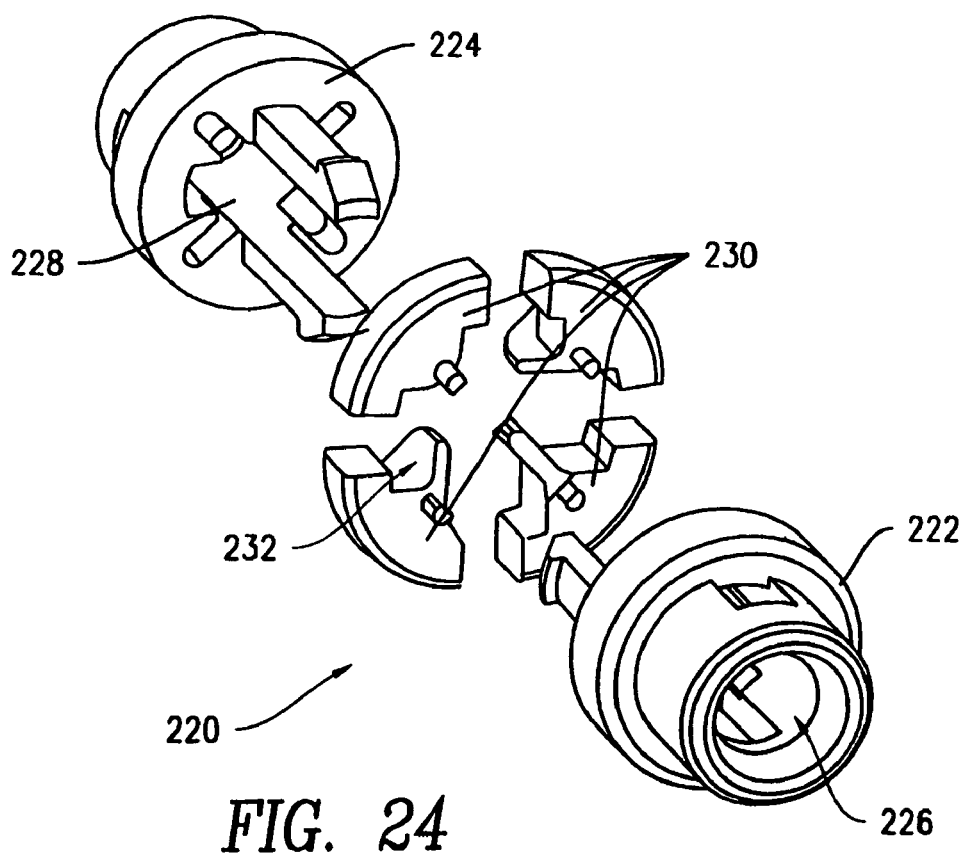
FIG. 24 shows an exploded view of the retaining mechanism of the fifth embodiment of the stent delivery system.

FIG. 23 shows stent delivery system 200 when assembled, with stent 150 disposed on stent delivery system 200 between mechanical retaining mechanisms 220.

The procedure for using stent delivery system 200 to implant stent 150 to maintain urethral patency is initiated by disposing stent 150 on catheter central portion 204, with all, or a portion of stent 150 located between mechanical retaining mechanisms 220. Mechanical retaining mechanisms 220 are then radially expanded to hold stent 150 on stent delivery system 200. After stent delivery system 200 is inserted into, and properly located in the prostatic urethra, the deployment catheter, rod, or scope is removed, which allows mechanical retaining mechanisms 220 to radially collapse to release stent 150 from stent delivery system 200 without changing the dimensions of stent 150. Stent delivery system 200 is then removed.

In regard to each embodiment illustrated above, the mechanisms which enable holding the stent to the stent delivery system, and anchoring the stent delivery system in the proper position before stent deployment, may be beneficially employed with any type of non-expanding stent.

Thus, while preferred embodiments of the devices and methods have been described in reference to the environment in which they were developed, they are merely illustrative of the principles of the invention. Other embodiments and configurations may be devised without departing from the spirit of the invention and the scope of the appended claims.

What is claimed is:

1. A system for delivering a non-expandable stent into the prostatic urethra of a patient, comprising a catheter; a controllable retainer mounted to said catheter, said retainer being capable of reversible expansion and contraction, and controlling means for controllably expanding and contracting said retainer, wherein said catheter, said retainer, and said controlling means are arranged such that, when said retainer is in a contracted state, a non-expandable stent situated coaxially around said catheter may be moved longitudinally along said catheter onto said retainer and off of said retainer and such that, when the stent is on said retainer and said retainer is in an expanded state, longitudinal movement of the stent off of said retainer is restricted.

2. The system according to claim 1, wherein said retainer includes an inflatable balloon.

3. The system according to claim 2, wherein said controlling means includes a first lumen extending longitudinally at least partially through the interior of said catheter and a radial port communicating with said first lumen, said balloon being positioned over said port.

4. The system according to claim 3, wherein said controlling means further includes pressurizing means for introducing a pressurized fluid into said first lumen.

5. The system according to claim 3, wherein said first lumen is closed at one end of said catheter.

6. The system according to claim 1, wherein said retainer includes a pair of mechanical retaining mechanisms spaced along said catheter so as to capture the stent therebetween when said pair of mechanisms are radially expanded, each of said pair of mechanisms including a retention member controllably movable radially outward from said catheter.

7. The system according to claim 6, wherein said catheter includes an interior longitudinal lumen; said retention member includes a deployment ramp extending into said lumen; and said system further includes a rod insertable into said lumen to selectively engage said deployment ramp and cause said retention member to be moved radially outward from said catheter.

8. The system according to claim 1, wherein said catheter includes a second lumen extending longitudinally entirely through the interior of said catheter and sized and shaped for receiving a guide wire.

9. The system according to claim 8, wherein said catheter includes a tip element at a distal end of said catheter, said tip element having a protrusion sealing said first lumen and an opening through said tip element communicating with said second lumen.

10. The system according to claim 1, wherein said catheter includes a second lumen extending longitudinally entirely through the interior of said catheter and sized and shaped for receiving visualization means.

11. The system according to claim 10, wherein said catheter includes a tip element at a distal end of said catheter, said tip element having a protrusion sealing said first lumen and an opening through said tip element communicating with said second lumen.

12. The system according to claim 1, wherein said catheter includes an interior longitudinal lumen and a radial port distally beyond said retainer and communicating with said lumen, said system further comprising a locating balloon positioned over said port, the spacing between said locating balloon and said retainer being such that said locating balloon can be inserted through the patient's urethra and into the patient's bladder and inflated and such that, when said catheter is subsequently withdrawn along the urethra to a position where said inflated balloon contacts the bladder neck, a stent retained on the catheter by the retainer is properly positioned within the prostatic urethra.

13. A combination comprising:
a non-expandable stent; and
a delivery system for said stent, including a catheter, an expandable and contractible retainer mounted to said catheter, said stent being positioned on said retainer, and controlling means for moving said retainer between an expanded state, in which said retainer engages said stent such that said stent is maintained on said catheter by said retainer, and a contracted state, in which said retainer is disengaged from said stent so as to permit the removal of said stent from said catheter.

14. The system according to claim 13, wherein said retainer includes an inflatable balloon.

15. The system according to claim 14, wherein said controlling means includes a first lumen extending longitudinally at least partially through the interior of said catheter and a radial port communicating with said lumen, said balloon being positioned over said port.

16. The system according to claim 15, wherein said controlling means further includes pressurizing means for introducing a pressurized fluid into said first lumen.

17. The system according to claim 15, wherein said first lumen is closed at one end of said catheter.

18. The system according to claim 15, wherein said catheter includes a tip element at a distal end of said catheter, said tip element having a protrusion sealing said first lumen and an opening through said tip element communicating with said second lumen.

19. The system according to claim 13, wherein said catheter includes a second lumen extending longitudinally entirely through the interior of said catheter and sized and shaped for receiving a guide wire.

20. The system according to claim 13, wherein said catheter includes a second lumen extending longitudinally entirely through the interior of said catheter and sized and shaped for receiving visualization means.

* * * * *